US009244060B2

(12) United States Patent
Roy et al.

(10) Patent No.: US 9,244,060 B2
(45) Date of Patent: *Jan. 26, 2016

(54) SITE LOCALIZATION AND METHODS FOR MONITORING TREATMENT OF DISTURBED BLOOD VESSELS

(75) Inventors: Josee Roy, Memphis, TN (US); Roger Harrington, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 405 days.

This patent is subject to a terminal disclaimer.

(21) Appl. No.: 12/411,666

(22) Filed: Mar. 26, 2009

(65) Prior Publication Data

US 2010/0247441 A1 Sep. 30, 2010

(51) Int. Cl.
*A61K 49/00* (2006.01)
*G01N 33/50* (2006.01)
*G01N 33/58* (2006.01)

(52) U.S. Cl.
CPC .......... *G01N 33/5091* (2013.01); *A61K 49/006* (2013.01); *G01N 33/58* (2013.01); *G01N 2800/32* (2013.01)

(58) Field of Classification Search
CPC ..................................................... A61K 33/06
USPC .................................................... 424/9.1, 9.2
See application file for complete search history.

(56) References Cited

U.S. PATENT DOCUMENTS

| 3,026,248 | A | 3/1962 | Noseworthy et al. | |
|---|---|---|---|---|
| 4,020,162 | A | 4/1977 | Ghilardi et al. | |
| 4,451,447 | A | 5/1984 | Kaplan et al. | |
| 5,605,687 | A | 2/1997 | Lee et al. | |
| 5,746,998 | A * | 5/1998 | Torchilin et al. | 424/9.4 |
| 7,582,680 | B1 | 9/2009 | Shi et al. | |
| 7,837,987 | B2 | 11/2010 | Shi et al. | |
| 2003/0118545 | A1 | 6/2003 | Shi et al. | |
| 2004/0214790 | A1 | 10/2004 | Borgens | |
| 2005/0069520 | A1 | 3/2005 | Shi et al. | |
| 2005/0181010 | A1 | 8/2005 | Hunter et al. | |
| 2007/0012323 | A1* | 1/2007 | Roy et al. | 128/898 |
| 2007/0258938 | A1* | 11/2007 | Roy et al. | 424/78.3 |
| 2008/0243049 | A1 | 10/2008 | Hardy | |
| 2008/0294089 | A1 | 11/2008 | Hardy | |

FOREIGN PATENT DOCUMENTS

| GB | 1250304 A | 10/1971 |
|---|---|---|
| GB | 1286351 A | 8/1972 |
| WO | 0128544 A | 4/2001 |
| WO | 02092107 | 11/2002 |

OTHER PUBLICATIONS

Material Safety Data Sheet: CARBOWAX™ Polyethylene Glycol 3350, Dow Chemical Canada, Inc., pp. 1-8, available at www.ccc-group.com/docs/msds/english/288850.pdf (2007).*
International Search Report and Written Opinion for U.S. Appl. No. PCT/US2010/028233 mailed on Oct. 4, 2010.
International Preliminary Report on Patentability (Sep. 27, 2011).
Simpson et al., "Intrathecal magnesium sulfate protects the spinal cord from ischemic injury during thoracic aortic cross-clamping,"; Anesthesiology (1994) vol. 81, pp. 1493-1499.
Lang-Lazdunski et al., "Prevention of ischemic spinal cord injury: comparative effects of magnesium sulfate and riluzole," Journal of Vascular Surgery (Jul. 2000); vol. 32; No. 1; pp. 179-189.
Ancill, R.J., "The blood volume of the normal guinea-pig," J. Physiol. (1956) I32, pp. 469-475.
Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.
Borgens R B and Bohnert D., "Rapid recovery from spinal cord injury after subcutaneously administered polyetheylene glycol," Journal of Neuroscience Research (2001); vol. 66, pp. 1179-1186.
Ditor D S et al., "Effects of polyethylene glycol and magnesium sulfate administration on clinically relevant neurological outcomes after spinal cord injury in the rat," Journal of Neuroscience Research (2007); vol. 85, pp. 1458-1467.
International Preliminary Report on Patentability (Nov. 4, 2008).
Turner, et al., "Magnesium gluconate offers no more protection than magnesium sulphate following diffuse traumatic brain injury in rats", Journal of the American College of Nutrition. 23(51 (2004), 541S-544S.
Muir, et al., "Magnesium for acute stroke (Intravenous Magnesium Efficacy in Stroke trial): randomised controlled trial.". The Lancet, 363(9407). (Feb. 7, 2004). 439-45.
Saver, et al., "Prehospital Neuroprotective Therapy for Acute Stroke: Results of the Field Administration of Stroke Therapy-Magnesium (FAST-MAG) Pilot Trial.", Stroke, 35(5). (2004). 106-108.
Bittner, et al., "Reconnection of severed nerve axons with polyethylene glycol.". Brain Research, 367(1-2), (1986), 351-355.
McIntosh, et al., "Magnesium protects against neurological deficit after brain injury.". Brain Research. 482(2). (1989). 252-260.
Shapiro, et al., "Oscillating field stimulation for complete spinal cord injury in humans: a Phase 1 trial". J. Neurosurg Spine, 2(1), (Jan. 2005), 3-10.
Resende, et al., Local transcutaneous electrical stimulation (TENS) effects in experimental inflammatory edema and pain, European Journal of Pharmacology 504(1) (2004). 217-222.
Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).
Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).
Kwon, et al. "Translational Research in Spinal Cord Injury: A Survey of Opinion from the SCI Community," Journal of Neurotrauma, 27, pp. 21-33 (Jan. 2010).
McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).
Journal of Spinal Cord Medicine, 34(6), 620-621 (2011).

* cited by examiner

*Primary Examiner* — Dennis J Parad
(74) *Attorney, Agent, or Firm* — Sorell Lenna & Schmidt LLP

(57) ABSTRACT

Methods for identifying defects in blood vessels and treating such defects are provided. The methods comprise administering to a patient a composition comprising a labeled delivery ligand capable of preferentially accumulating at or near blood vessels defects. In some embodiments, the delivery ligand may carry one or more active agents to the defect.

18 Claims, 6 Drawing Sheets

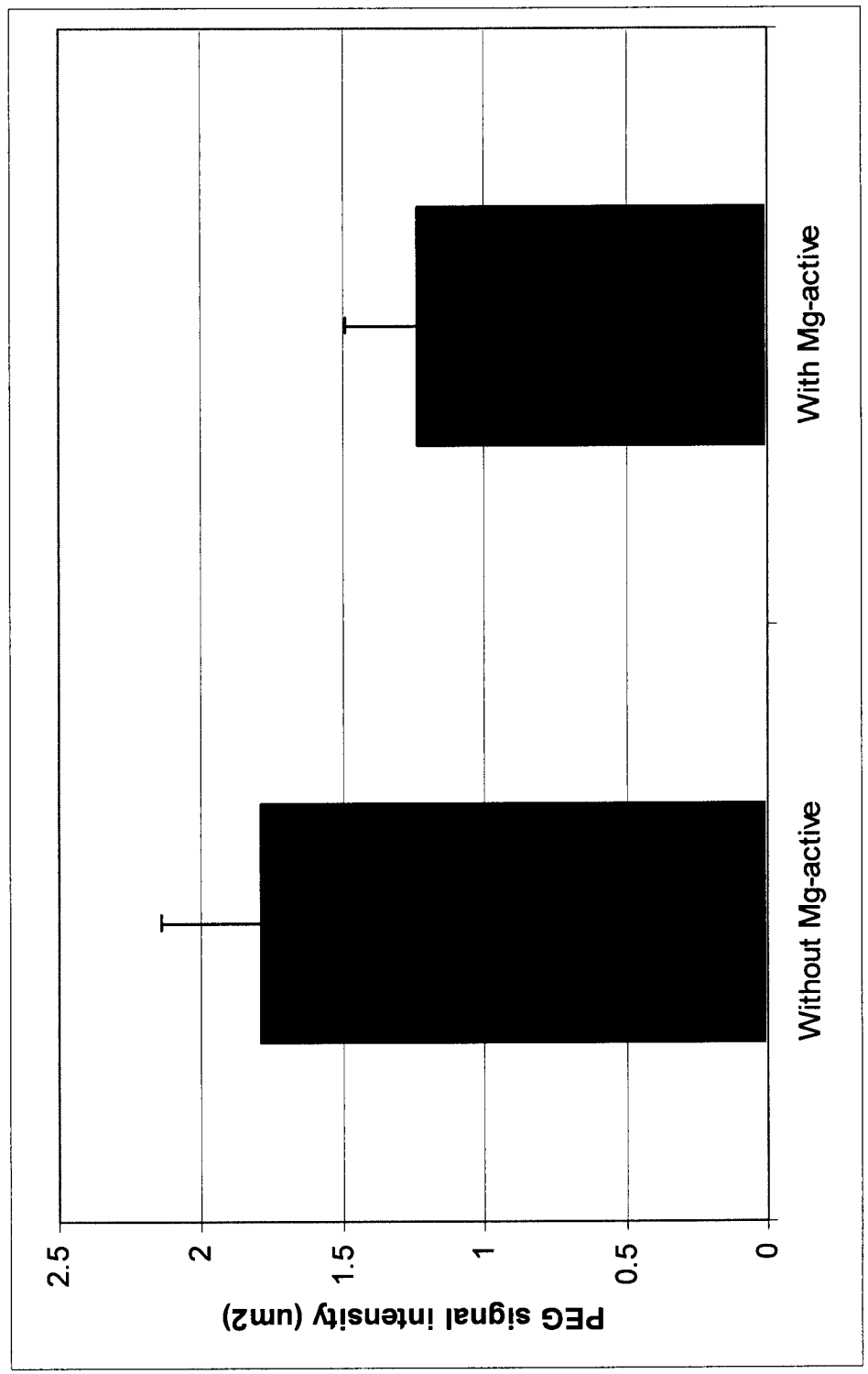

SITE LOCALIZATION AND METHODS FOR MONITORING TREATMENT OF DISTURBED BLOOD VESSELS

FIELD OF THE INVENTION

This invention relates to methods and compositions for identifying defects in blood vessels and monitoring their treatment.

BACKGROUND OF THE INVENTION

Bleeding, technically known as hemorrhaging, is the loss of blood from the circulatory system. Bleeding occurs when a blood vessel within the body is ruptured. The vessel may be ruptured as a result of a physical trauma or non-traumatic causes such as an aneurysm. A ruptured vessel can result in severe internal bleeding, which can lead to shock or even death. For example, around half of all people who experience a ruptured aneurysm die, either within the first day or the next three months. About fifty percent of the survivors are usually left with lifelong disabilities. In addition, blood vessels may become leaky due to diseases and conditions that cause swelling and inflammation such as chronic pain or angiogenesis such as cancer. Leaky vessels can contribute to exacerbate pain and the progression of the disease.

Accordingly, there is a need in the art for a method of detecting defects in blood vessels and treating of such defects.

SUMMARY OF THE INVENTION

In one aspect, methods of identifying a defect in a blood vessel, such as a leak, hole or rupture, are provided. Such methods comprise administering to a patient a composition comprising a labeled delivery ligand that accumulates preferentially at the site of the blood vessel defect, if one is present, and enables the determination of the precise location and severity of the defect. The amount of the delivery ligand may depend on the strength of the label and ability of the delivery ligand to find and to accumulate at the site of the blood vessel defect.

In another aspect, methods of monitoring active agent delivery to defects in blood vessels are provided. Such methods comprise administering to a patient a composition comprising a labeled delivery polymer and one or more active agents bound to the delivery ligand and detecting the labeled delivery ligand to determine the dose of active agent that was delivered within the affected organ.

In yet another aspect, methods of monitoring the effectiveness of a treatment for damaged blood vessels are provided. Such methods comprise identifying the presence and severity of a blood vessel defect, administering the composition comprising an active agent with blood flow modifying activity and re-evaluating the severity of the defect.

In some embodiments, the labeled delivery ligand may be selected from a hydrophilic or amphipathic polymer such as polyethylene glycol (PEG), and the active agent is a metal ion.

In some embodiments, the composition can comprise up to 60% weight per volume of PEG and about 0.1% and about 20% weight per volume of an active agent that can form ionic bonds with the delivery ligand.

In yet another embodiment, the composition is administered intravenously.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 2a presents a graph comparing signal intensity of a labeled ligand at the site of a blood defect following treatment with and without an active agent.

Figure 1:
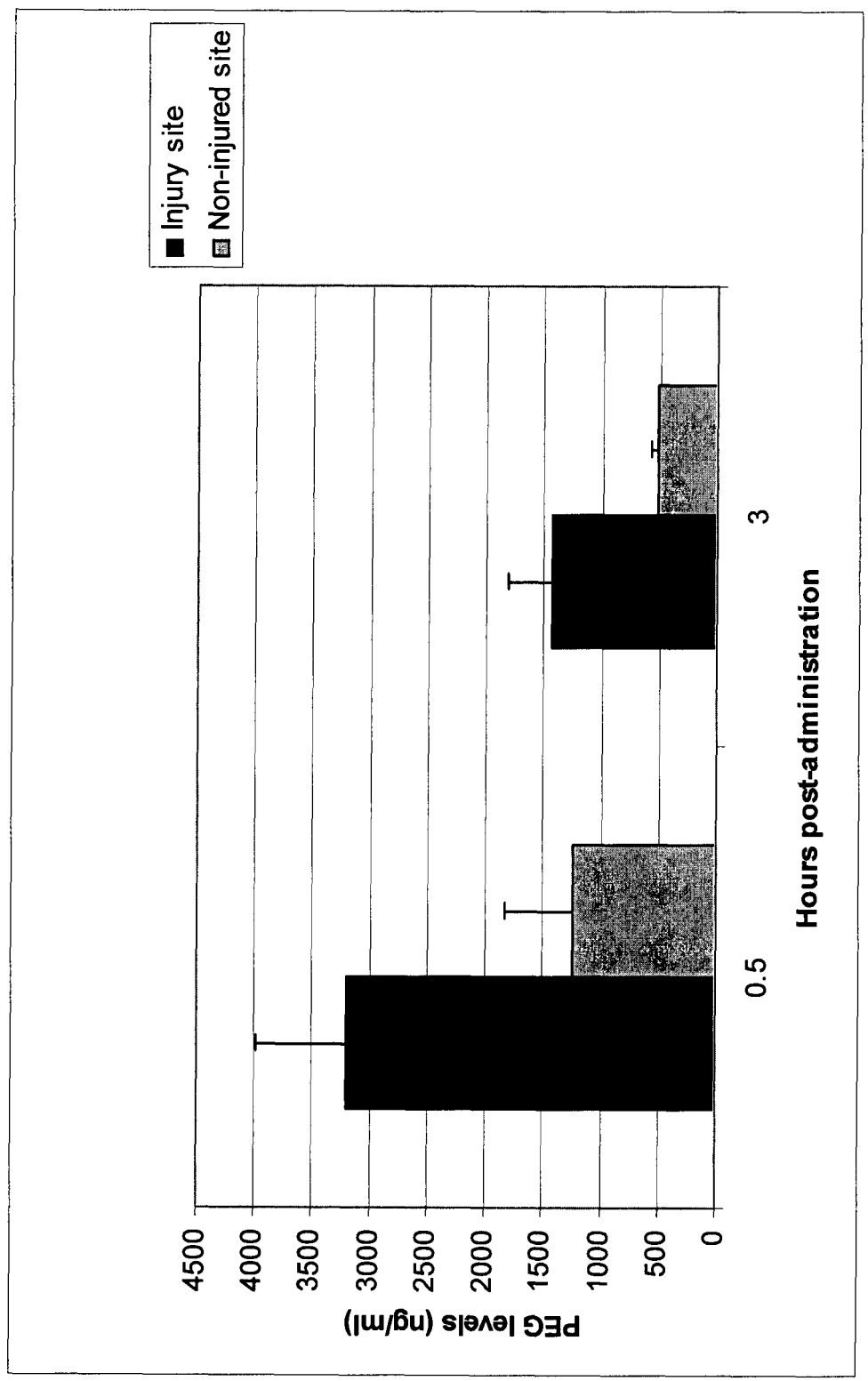
FIG. 1 presents a graph showing that PEG accumulates preferentially at the site of a blood vessel defect within an injured organ.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION OF THE INVENTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

In one aspect, methods of identifying a defect in a blood vessel, such as a leak, hole or rupture, are provided. Such methods comprise administering to a patient a composition comprising a labeled delivery ligand. The amount of the delivery ligand may depend on the strength of the label or ability of the delivery ligand to find and to accumulate at the site of the blood vessel defect. The amount of the labeled ligand that is delivered to the patient may be adjusted, for example, by changing the ligand concentration in the composition, utilizing ligands with different molecular weight, or varying the dose of the composition.

By way of a non-limiting example, the concentration of the delivery ligand in the instant compositions may include up to 60% weight to volume, i.e. 60 gm of compound to 100 ml solution. In some embodiments, the concentration of the delivery ligand may be below 40% weight per volume. In other embodiments, the concentration of the delivery ligand may range between about 15 and 60 percent weight per volume. Suitable compounds for use as delivery ligands in instant compositions would have a molecular weight between about 100 and 20,000 DA, between about 1000 to 9000 DA, or between about 2,000 DA and about 4,000 DA. The dose of the instant composition may range between about 0.01 to 10 ml of composition per 1 kg of patient's weight or between about 0.01 and 1 ml of composition per 1 kg of patient's weight.

Suitable delivery ligands in instant compositions may meet the following criteria: 1) they are water soluble; 2) they are rapidly cleared from the intact blood vessels and excreted; 3) they accumulate preferentially where there are defects in blood vessels; and 4) they possess hydrophilic properties. In addition, suitable ligands may include chelation sites suitable for ionic binding with labels as well as with cations, as is explained in detail below.

As noted above, it is desirable that the delivery ligands are rapidly excreted from the body when the blood vessels are intact. Accordingly, delivery ligands can have a half-life of less than 3 hours, less than 2 hours or less than 1 hour. The rate of excretion, or half-life, of a ligand is related to the molecular weight of the ligand, with higher molecular weight ligands having longer half-lives. In contrast, the half-life of a label depends on the detection technology. Also, for the same molecular weight, hydrophilic ligands have shorter half-lives than more hydrophobic ligands. Hydrophilic ligands that can be excreted mostly unchanged through urine have shorter half-life than ligands that requires some transformation before excretion. For example, since 24,000 DA is the cut-off for glomerular filtration, any ligand heavier than 24,000 DA needs to be degraded to some extent before it can be excreted, which adds to its half-life. Accordingly, delivery ligands may be selected from polymers with hydrophilic properties having a molecular weight of less than about 24,000 DA.

Ligands or compounds with hydrophilic properties may be selected from a hydrophilic or an amphipathic polymer. The term "hydrophilic polymer," as used herein, means any macromolecule (molecular weights of 200 daltons and greater) which exhibits an affinity for or attraction to water molecules and which comprises multiple instances of an identical subunit ("monomer") connected to each other in chained and/or branched structures. The hydrophilic polymer may be a synthetic or naturally occurring hydrophilic polymer.

Naturally occurring hydrophilic compounds include, but are not limited to: proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; methyl cellulose, sodium carboxylmethyl cellulose and activated polysaccharides such as dextran, starch and derivatives.

Useful synthetic hydrophilic compounds include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), poly(polyethylene glycol methacrylate), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid, propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline); polyvinylamines and derivatives.

The term "amphipathic polymer," as used herein, refers to any macromolecule (molecular weights of 200 daltons and greater) which have localized quantum variations in charge giving rise to polar substructures and non-polar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic). Suitable amphipathic polymers include, but are not limited to, poloxamer P-188, polyetherester copolymers such as polyethylene glycol and polybutylene terephthalate copolymers, polyethylene glycol and polypropylencoxide copolymers, polyethylene glycol, polypropylene glycol block copolymers and derivatives.

The amphipathic polymers also include a family of polyetheramines known as Jeffamine®. These polyetheramines contain primary amino groups attached to the end of a polyester backbone, which is typically based on propylene oxide (PO), ethylene oxide (EO), or a mixture thereof. The Jeffamine® family includes monamines, diamines, triamines and secondary amines. Jeffamine® may be procured from Huntsman Corporation, headquartered in The Woodlands, Tex.

In some embodiments, the delivery polymer may comprise polyethylene glycol (PEG). PEGs of different molecular weights may be obtained from, for example, Sigma-Aldrich, St. Louis, Mo., USA.

The delivery ligands may be labeled with a compound, referred to herein as a label, capable of providing a signal detectable, and they can be quantifiable, by medical imaging techniques, such as MRI, X-Ray, CT scan, PET scan, fluoroscopy, luminescence and so forth. Examples of suitable labels include, but are not limited to, stable isotopes such as $^{13}C$, $^{35}Cl$, $^{37}Cl$ $^{10}B$, $^{3}He$, $^{15}N$, $^{17}$ or $^{18}O$, $^{129}X$ and radioisotope-containing moieties such as $^{18}F$, $^{3}H$, $^{124}I$, $^{125}I$, $^{129}I$, or $^{131}I$, $^{35}S$, $^{14}C$, $^{11}C$, $^{32}C$, or $^{33}C$, $^{133}X$ mass-tags, biotinylated and fluorescent labels and dyes. Accordingly, following administration of instant compositions, the existence, precise location and extent of a defect may be determined using medical imaging techniques to visualize where, and if, the delivery ligand accumulates. The instant compositions may also be administered following the treatment in order to monitor a patient's progress.

In another aspect, methods of monitoring active agent delivery to the site of blood vessel defects are provided. Such methods include administering to a patient a labeled as a single composition or as multiple compositions. If the labeled ligand and the one or more active agent are administered as separate compositions, they can be administered simultaneously or consecutively. The dose of the composition comprising the active agent may be estimated based on patient's weight using the ratio of about 0.1 ml to 10 ml of composition per 1 kg of patient's weight or between about 1 to 8 ml of composition per 1 kg of patient's weight. The dose of the separate composition comprising the labeled agent may be about 0.01 to 10 ml of composition per 1 kg of patient's weight or between about 0.01 to 1 ml of composition per 1 kg of patient's weight.

The term "active agent," as used herein, refers to a chemical element or compound that alleviates signs or symptoms of the blood vessel defect or, otherwise, needs to be delivered to the site of such defect. The concentration of active agents in the instant compositions may range between about 0.1% to about 20% weight per volume, and more preferably between 0.8 and 20% weight per volume.

In some embodiments, suitable active agents may be selected from blood flow modifying agents, such as, for example, magnesium, potassium, nitric oxide, corticotropin-releasing hormone, parathyroid hormone, bradykinin molecules and derivatives.

The interactions between the delivery ligand and one or more active agents may be defined as a "chelation" like effect. Cations of the active agent may form electrostatic attraction to certain heteroatoms of the delivery ligand, for example, N, O, and S atoms, of the delivery ligand. Such binding sites are referred herein as chelation sites. For example, although the hydrophilic polymer PEG as a whole is non-ionic, the free electron pairs on the heteroatom on the PEG chains impart an anionic character to the polymer that can bind to a metal ion with blood flow modifier activity such as magnesium chloride through cations like $Mg^{2+}$ or $MgCl^+$.

In various embodiments, the active agent comprises a magnesium compound. Various magnesium salts may provide a source for the magnesium compounds. Magnesium salts can include, but are not limited to, magnesium sulfate, magnesium carbonate, magnesium chloride, magnesium oxide and magnesium hydroxide. These compounds are readily available commercially from, for example, Sigma Aldrich, St. Louis, Mo., USA.

In some embodiments, the label may also bind to chelation sites present on the ligand and be selected from stable isotopes or radioisotopes, including, but not limited to derivatives of alkali metals such as calcium, lithium, cesium, barium and magnesium; derivatives of transition metals such as copper, iron, molybdenum, zinc, cobalt, silver, iridium, osmium, strontium, technetium, tungsten, platinum and gold; as well as radioactive lanthanides and actinides including $^{141}Ce$, $^{165}Dy$, $^{253}Es$, $^{169}Er$, $^{159}Gd$, and $^{166}Ho$.

The number of chelation sites in a delivery ligand depends on its molecular weight as well as the type of subunits that make up the ligand. The delivery ligands are composed of repeating sub-units of one or more types, at least some of which include chelation sites. Delivery ligands with higher molecular weight are composed of a higher number of sub-units, and thus they are more likely to have a higher number of chelation sites than delivery ligands with lower molecular weight. Furthermore, some subunits may have several chelation sites, whereas others may have no chelation sites. Accordingly, as a general rule, the concentration of the delivery ligand with higher molecular weight in the composition may be lower than the concentration of the delivery ligand comprising the same sub-units and having a lower molecular weight. The type of ionic bond can vary including electron sharing between one or more metal ions and one or more subunits of the delivery ligand. The metal counterion may also participate in the formation of the complex with the delivery ligand.

Following administration of the composition, the labeled delivery ligand may be visualized to determine whether the active agent has been delivered to its target, as well as the amount of active agent that has been delivered. The amount of the active agent delivered to the site of blood vessel defects can be evaluated from the amount of the labeled ligand administered, the amount of the labeled ligand found at the site of blood vessel defects and the ratio between the labeled ligand and active agent administered. The amount of active agent delivered to the site of a blood vessel defect can be evaluated from the amount of the labeled ligand administered, the amount of the labeled ligand detected at the site of the defect and the ratio between the labeled ligand and active agent administered. The ratio between the labeled ligand and active agent administered will be dependent on the time of evaluation as it relates to the detection technology, the half-life of the label and the time required for the active agent to reach the targeted sub-compartment within the injured organ or the extra-cellular fluid surrounding the injured tissue. The type of label, the timing of the evaluation and the number of administrations may influence the calculation of the amount of active agent that has accumulated at the targeted site. For example, when a composition comprising 0.8 mg/ml of magnesium and 1.5 g/ml PEG3350 was administered intravenously following a mechanical injury to the spinal cord in rats, about 1.4 ug/ml of PEG was found at the site of blood defect within the spinal cord which correlated to 14 ug/ml of magnesium in the cerebrospinal fluid. Knowing the amount of the active agent delivered to the injury site is extremely beneficial as it provides a physician with ability to improve the safety and efficacy of the treatment.

Instant methods also enable monitoring the progress of treatment. At certain time intervals following the commencement of treatment, additional amounts of the delivery ligands with or without the active agent may be administered to the patient being treated. If the defect is still present, the delivery ligands will accumulate at the site of the defect and will be visualized, thus enabling a physician to determine whether the defect is healing, is getting worse, or is staying the same. Additionally, if any new defects form following the commencement of treatment, they will also be detected. For example, following a mechanical injury to the spinal cord in rats, intravenous administration of a composition comprising the labeled PEG3350 and the magnesium-active agent led to a decrease of about 31% in the label signal at the site of blood defect which correlated with a reduction of the hemorrhage severity by about 47% relative to the intravenous administration of PEG alone compositions.

In addition to the delivery ligand and the active agents, the instant compositions may include one or more pharmaceutically acceptable carriers. The instant compositions may include excipients such as solvents, binders, fillers, disintegrants, lubricants, suspending agents, surfactants, viscosity increasing agents, buffering agents, antimicrobial agents, among others. Many different pharmaceutically acceptable carriers and excipients are known and disclosed, for example, in Remington's Pharmaceutical Sciences, Lippincott Williams & Wilkins; 21 edition (May 1, 2005).

Having now generally described the invention, the same may be more readily understood through the following reference to the following example, which is provided by way of illustration and is not intended to limit the present invention unless specified.

EXAMPLE

Figure 3:
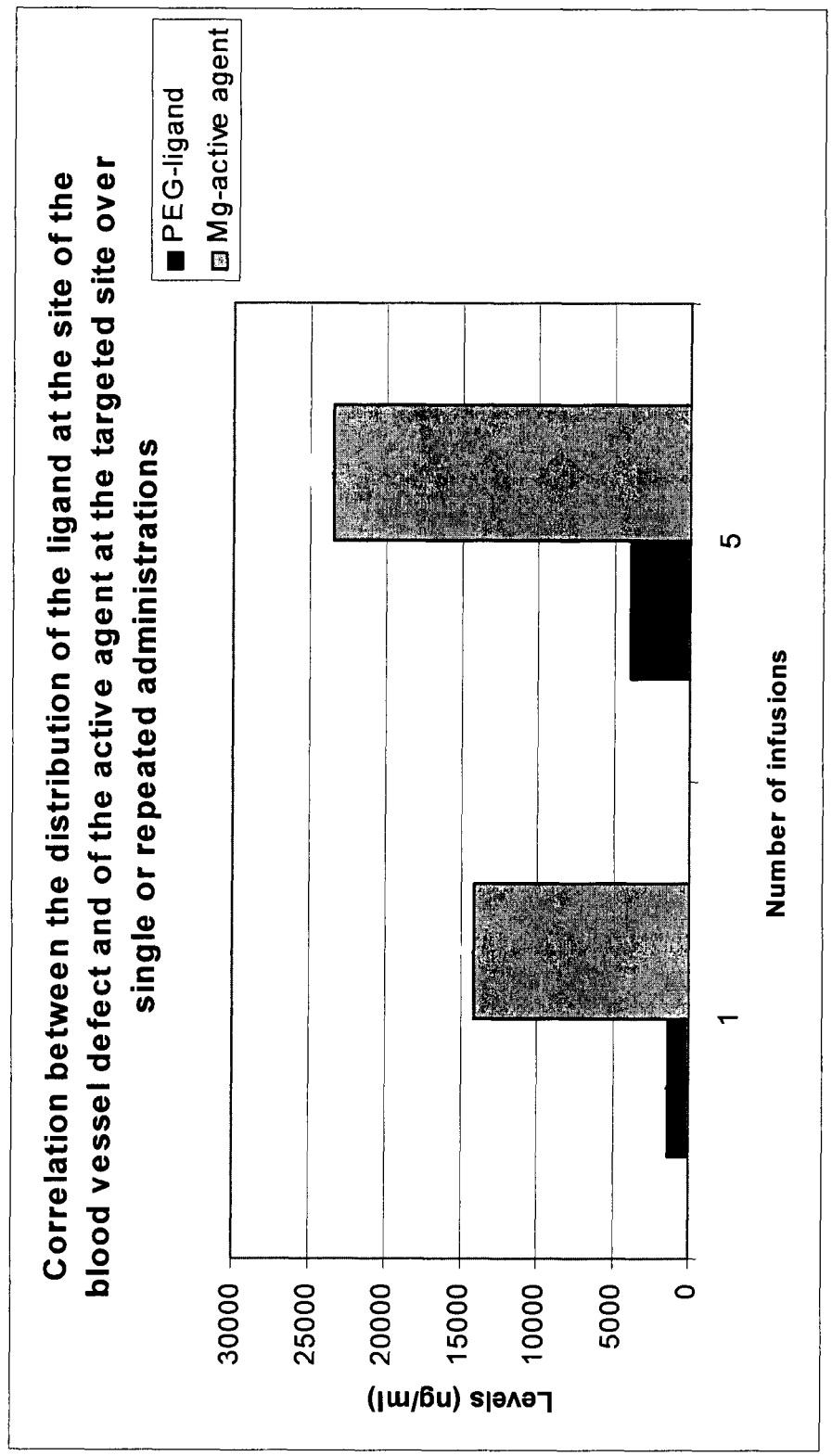
FIG. 3 presents a graph showing a correlation between the distribution of a ligand at the site of a blood defect and of the active agent within a target organ.

Methods and Tests Pertaining to FIGS. 1, 3-4:

Female Sprague-Dawley rats (Harlan Sprague-Dawley, Indianapolis, Ind.), weighing 250-300 grams each were given free access to food and water before the experiment. The animals were anesthetized with ketamine (80 mg/kg) and xylazine (10 mg/kg). Brain temperatures were monitored using a rectal thermometer. The animals' body temperature was maintained at 37° C. by using a water-jacketed heating pad. Brain temperature was monitored for 1 hour prior to injury to 6 hours following injury and was recorded at 30-minute intervals.

Young adult female Sprague-Dawley rats received a spinal cord contusion using the Precision Systems and Instrumentation, LLC (Fairfax Station, Va.) pneumatic impactor. Prior to surgery, rats were assigned to different treatment groups based on a randomized block design so that on any given surgery day all treatment groups were included. The rats were anesthetized with ketamine (80 mg/.kg) and xylazine (10 mg/kg) before laminectomy was performed at the $10^{th}$ thoracic vertebra ($T_{10}$). The vertebral column was stabilized with angled clamps on the upper thoracic (T8) and lumber (T11) levels and the impactor with a tip diameter of 2 mm was delivered at approximately 150 kdynes onto the exposed, intact dura overlying the dorsal spinal cord. The impactor was immediately removed, the wound irrigated with saline and the muscle and skin openings sutured together.

Two hours following injury, 0.8% magnesium in 3350 formulations was administered by intravenous infusion of 5 mL/kg over a 30-min period. For repeated infusions, an interval of 6 hours was used between infusions and the right jugular vein was cannulated with PE 50 tubing. The cannula was secured through the back of the neck and capped between infusion periods. Animals were re-anesthetized for re-administration of compounds. The contents of the infusion vials were blinded to the investigators performing both the infusions and the analyses.

At various time points after infusion, cerebrospinal fluid and/or blood samples and/or spinal cord tissue with and without the injury site were collected. The blood samples were processed to serum for the magnesium assay or to plasma for the PEG assay.

Serum and CSF samples were analyzed for magnesium concentrations by the Clinical Pathology Department at WIL Research Laboratories, LLC, 1407 George Road, Ashland, Ohio 44805. Serum and CSF samples were reacted with xylidyl blue in an alkaline solution containing ethylenegly-col-bis(2-aminoehtylether)-N,N,N',N'-tetraacetic acid (EGTA) to form a purple chromophore. The formation of the chromophore (and consequently a reduction of the xylidyl blue) is proportional to the concentration of $Mg^{2+}$, measured by the instrument as a decrease in the xylidyl blue absorbance (600 nm). A Hitachi 912 clinical chemistry analyzer assay was used for the determination of magnesium in serum and CSF.

Tissue and plasma concentrations of PEG-3350 in rat plasma were measured using a validated high performance liquid chromatograpy tandem mass spectrometry (HPLC/MS/MS) method in positive electrospray ionization mode. The method for the determination of PEG-3350 used acetonitrile to de-proteinize 200 μL of plasma. Following centrifugation of the plasma or tissue homogenate, the supernatant fraction from each sample was concentrated by evaporation and reconstituted with mobile phase A prior to analysis. The samples were analyzed with an HPLC/MS/MS assay using a Thermo Hypersil ODS column. The peak areas of PEG-3350 and the theoretical concentrations of calibration standards were fit to the ln-quadratic function, excluding the origin.

Methods and Tests Pertaining FIG. 2:

Male Sprague-Dawley Rats were anesthetized and placed in a prone position on a stereotaxic frame. A T9/10 laminectomy was performed and animals were contused at a displacement of 1.5 mm with the Ohio State University impactor.

Soon after injury PEG-biotin or magnesium in a PEG3000-biotin formulations were administered by intravenous infusion over a 10 min period. The contents of the infusion vials were blinded to the investigators performing both the infusions and the analyses.

Figure 2B:
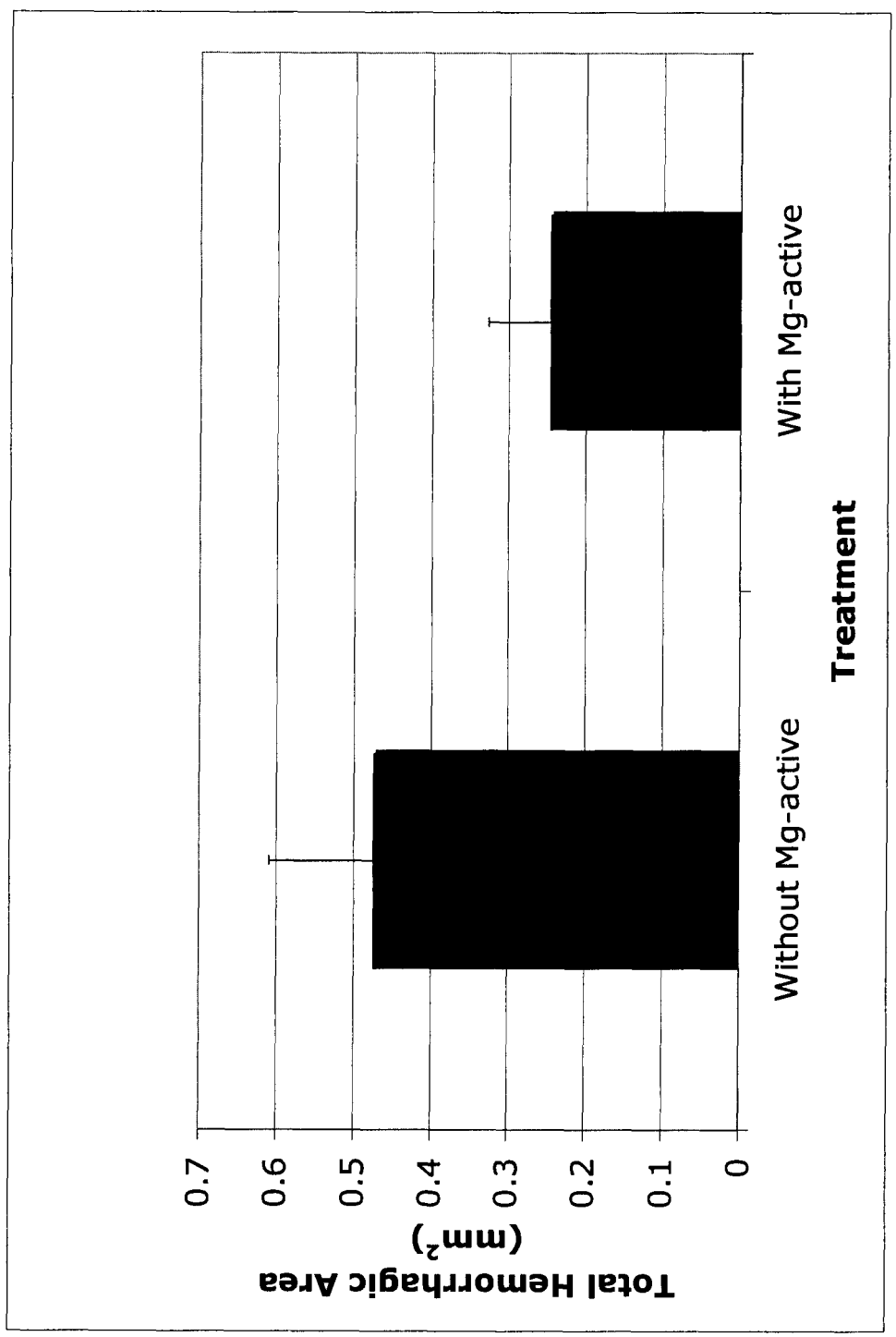
FIG. 2b presents a graph comparing hemorrhage severity at a site of injury following treatment with and without an active agent.

At 24 hours after infusion, the tissue we extracted and processed for histological evaluation (FIG. 2a) or functional analysis (FIG. 2b).

For the histology analysis presented at FIGS. 1 and 2, the cords were harvested at the indicated timepoints, cut horizontally at 20 um thickness and processed using the calorimetric ABC kit that includes reaction with avidin-peroxidase complexes and the peroxidase susbrate DAB leading to the development of a brown color where the biotin molecules (here the PEG-biotin) are located.

The following method describes the functional analysis or evaluation of the extent of hemorrhage at the injury site. The animals were decapitated and a 15 mm segment of the spinal cord centered around the hemorrhagic site was collected and frozen and cyrosectioned at a thickness of 20 um. Eleven sections per cord were selected for analysis: the epicentre of injury, and the sections rostral and caudal 400 um, 800 um, 1600 um, 2800 um, and 3200 um. The slides were cover slipped and color images of the spinal cords were obtained at 5× objective using a Leica light microscope. The red channel (representing bleeding into the tissue) was captured on a greyscale image, and the intensity threshold was set at 230 across all images to remain consistent throughout. The spinal cords, excluding the dura and blood trapped underneath, were circled in green. The overlapping signals of expressed red and circled green was highlighted with blue using the Overlay Math function under Image from the toolbar in Sigma Scan and the total area of blue signal was measured as the extent of hemorrhage.

Results:

PEG preferentially accumulates at the site of blood vessel defect within the injured organ.

Quantitative evaluation of PEG spinal tissue levels using HPLC/MS/MS assay also indicated that PEG accumulates preferentially at the site of blood vessel defect with PEG tissue levels three fold higher at the site of injury than one 1-cm above the site of injury when evaluated 30 minute post-administration. Although the level of PEG decrease over time in the cord, there was still a 3-fold difference between the PEG levels found at the injured site relative to the non-injured site 3 hours post-administration. These results are presented in FIG. 1.

The signal derived from the labeled PEG is indicative of the treatment effect at the site of the blood defect.

Referring to FIG. 2a, histological DAB staining of the injured spinal cord indicated that the labeled area correspond to about 1.79 um$^2$ following parenteral administration of the labeled PEG solution as compared to an labeled area of about 1.24 um when the magnesium-active agent was added to the PEG solution.

Quantitative morphometric analysis of the hemorrhagic signal within an area covering 3.2 mm$^2$ of the epicenter of the injury site is presented in FIG. 2b. Administration of a PEG solution led to bleeding detected in an area size of 0.47 mm. The extent of the bleeding area was reduced to 0.25 mm$^2$ when magnesium-active agent was added to the PEG solution.

Correlation between the distribution of the ligand at the site of blood defect and of the active agent within the target organ.

Following a single intravenous administration of the magnesium in PEG formulation, 1.4 ug/ml of PEG was found at the site ob blood defect in the spinal cord and 14 ug/ml of Magnesium in the cerebrospinal fluid for a ratio of 1:10. Following five repeated infusions with a 6-hour interval between infusions, 4 ug/ml of PEG was found at the site ob blood defect in the spinal cord and 24 ug/ml of Magnesium in the cerebrospinal fluid for a ratio of 1:6. It is possible that the ratio PEG:Magnesium found at the site of blood defect may vary over time after the injury and over repeated infusions based on tissue healing and clearance kinetics of the ligand and/or active agent.

PEG and exogenous magnesium are rapidly cleared from the systemic circulation and thus are not indicative of their accumulation at and around blood vessel defects.

Figure 4A:
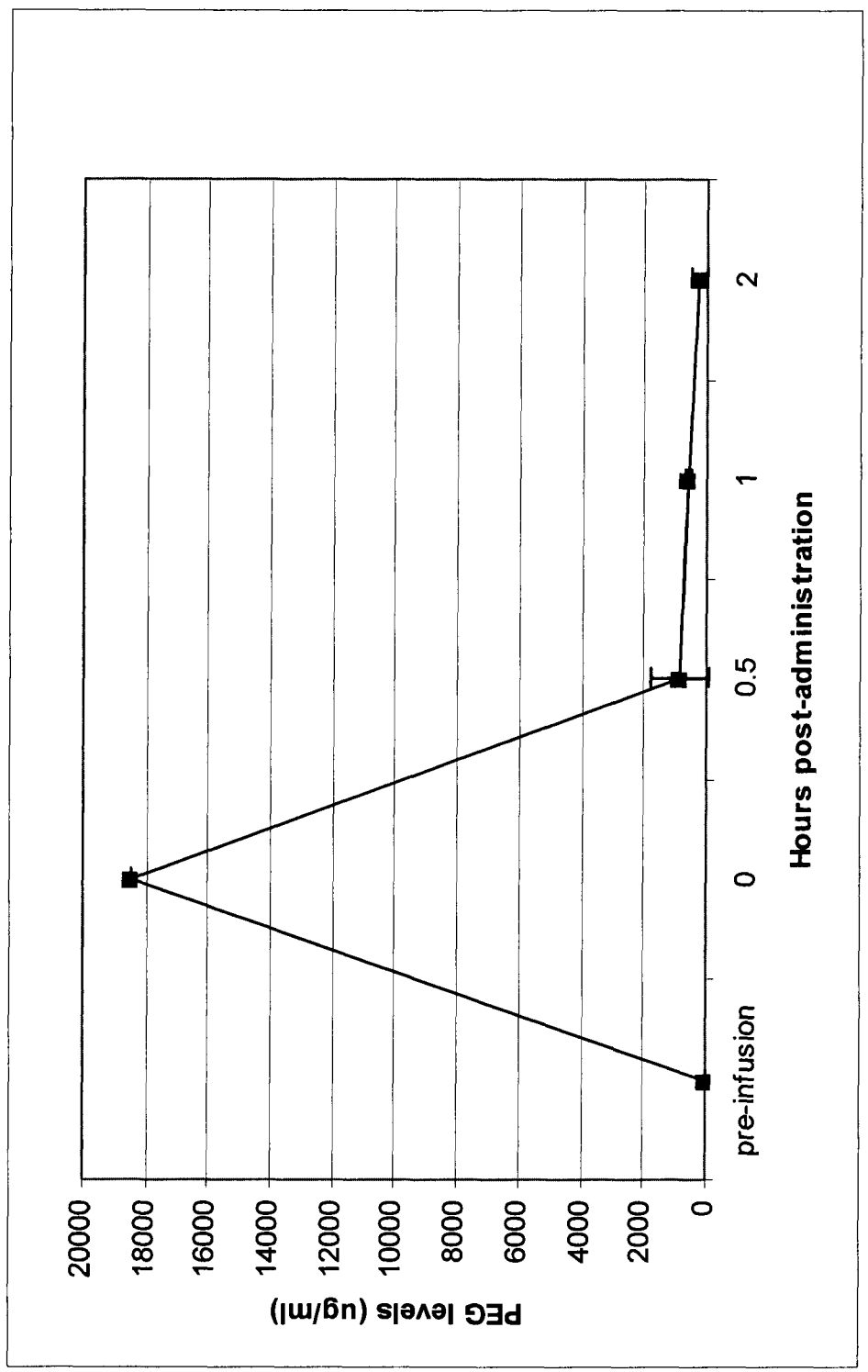
FIG. 4a presents data showing that PEG is cleared rapidly from the systemic compartment following tissue injury.
Figure 4B:
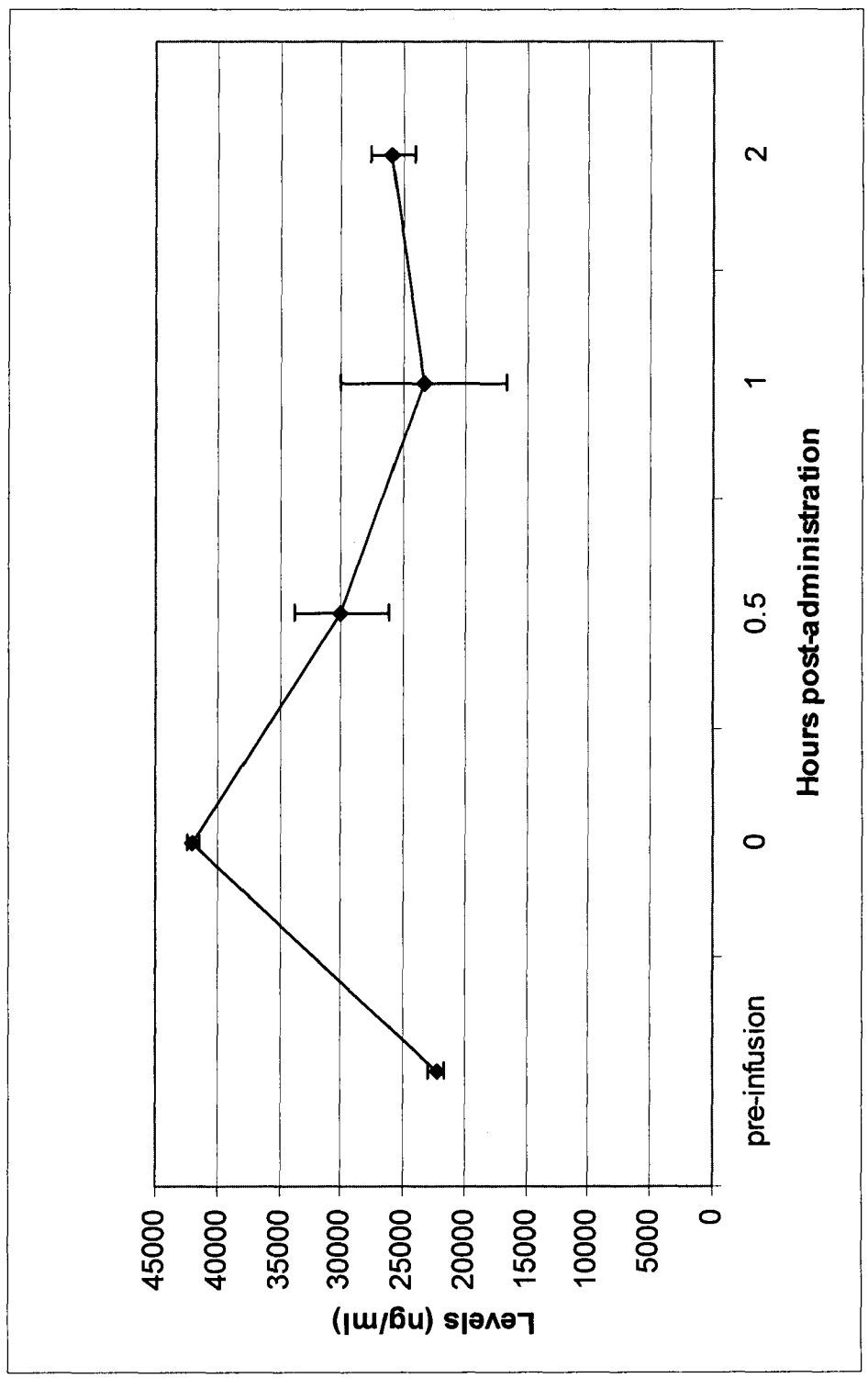
FIG. 4b presents data showing that exogenous magnesium is cleared rapidly from the systemic compartment following tissue injury.

Referring to FIGS. 4a and 4b, in injured animals, Cmax values for the PEG plasma and Magnesium serum levels were observed at the end of the infusion and levels decreased rapidly to baseline level within 30 to 60 minutes post-infusion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A method of determining a size of a hemorrhage of an injured tissue in a patient, the method comprising:
   administering to the patient a dose of a composition comprising a labeled delivery ligand comprising polyethylene glycol (PEG) having a molecular weight of between about 1000 DA and about 9,000 DA, wherein the polyethylene glycol comprises about 15% to about 60% weight per volume of the delivery ligand and the composition comprises about 0.8% weight per volume of a magnesium salt and the delivery ligand and the magnesium salt accumulate at or near the hemorrhage;
   detecting the labeled delivery ligand at or near the hemorrhage;
   determining an initial ratio of PEG to magnesium salt accumulated at or near the hemorrhage where the ratio of PEG to magnesium salt is 1 to 10;
   administering five additional doses of the composition; and
   determining a final ratio of PEG to magnesium salt accumulated at or near the hemorrhage where the final ratio of PEG to magnesium salt is 1 to 6, which indicates a reduction in the size of the hemorrhage, and the injured tissue comprises a spinal cord.

2. The method of claim 1, wherein the polyethylene glycol comprises about 40% weight per volume of the delivery ligand.

3. The method of claim 1, wherein the delivery ligand is hydrophilic or amphipathic.

4. The method of claim 1, wherein the composition is administered intravenously.

5. The method of claim 1, wherein the delivery ligand comprises polyethylene glycol (PEG) having a molecular weight of between about 2000 DA and about 4,000 DA.

6. The method of claim 1, wherein the magnesium salt comprises magnesium sulfate, magnesium carbonate, magnesium chloride, magnesium hydroxide, magnesium oxide or a combination thereof.

7. A method of monitoring active agent delivery to injured tissue having a hemorrhage in a patient, the method comprising:
   administering to the patient a dose of a composition comprising a labeled delivery ligand comprising polyethylene glycol (PEG) having a molecular weight of between about 1000 DA and about 9,000 DA and one or more active agents, wherein the polyethylene glycol comprises about 15% to about 60% weight per volume of the delivery ligand and the one or more active agents comprises about 0.8% weight per volume of magnesium and the delivery ligand and the one or more active agents accumulate at or near the hemorrhage;
   detecting the labeled delivery ligand at or near the hemorrhage;
   determining an initial ratio of PEG to magnesium accumulated at or near the hemorrhage where the ratio of PEG to magnesium is 1 to 10;
   administering five additional doses of the composition; and
   determining a final ratio of PEG to magnesium accumulated at or near the hemorrhage where the final ratio of PEG to magnesium salt is 1 to 6, which indicates a reduction in the size of the hemorrhage.

8. The method of claim 7, wherein the delivery ligand is hydrophilic.

9. The method of claim 7, wherein the magnesium comprises magnesium sulfate, magnesium carbonate, magnesium chloride, magnesium hydroxide, magnesium oxide or a combination thereof.

10. The method of claim 9, wherein the composition is injectable.

11. The method of claim 7, wherein the polyethylene glycol comprises between about 40 to about 60% weight per volume of the delivery ligand.

12. A method of monitoring treatment of a hemorrhaging blood vessel in a patient, the method comprising administering to the patient a dose of a composition comprising about 15 to about 60% weight per volume of labeled PEG having a molecular weight of from about 2000 DA to about 4,000 DA and about 0.8% weight per volume of one or more active agents comprising magnesium;

detecting the labeled PEG at or near the hemorrhage;

determining an initial ratio of PEG to magnesium at or near the hemorrhage where the ratio of PEG to magnesium is 1 to 10;

administering five additional doses of the composition; and determining a final ratio of PEG to magnesium at or near the hemorrhage where the final ratio of PEG to magnesium salt is 1 to 6, which indicates a reduction in the size of the hemorrhage.

13. The method of claim 1, wherein the delivery ligand comprises a label comprising biotin.

14. The method of claim 1, wherein the PEG comprises PEG 3350.

15. The method of claim 1, wherein the composition comprises about 0.8% weight per volume of magnesium chloride.

16. The method of claim 7, wherein the injured tissue comprises a spinal cord.

17. The method of claim 1, wherein the labeled delivery ligand is labeled with fluorescent labels and/or dyes.

18. The method of claim 1, wherein the time period between administering each of the five additional doses of the composition is 6 hours.

* * * * *